(12) United States Patent
Ein-Gal

(10) Patent No.: US 6,517,537 B2
(45) Date of Patent: Feb. 11, 2003

(54) ELECTROSURGICAL SYSTEM

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 48 days.

(21) Appl. No.: 09/863,484

(22) Filed: May 22, 2001

(65) Prior Publication Data

US 2002/0019655 A1 Feb. 14, 2002

(51) Int. Cl.⁷ .................................................. A61B 18/18
(52) U.S. Cl. ............................................ 606/41; 607/101
(58) Field of Search ............................. 606/34, 41, 42; 607/101, 102

(56) References Cited

U.S. PATENT DOCUMENTS

| | | | |
|---|---|---|---|
| 5,366,490 A | | 11/1994 | Edwards et al. |
| 5,370,675 A | * | 12/1994 | Edwards et al. ............... 606/32 |
| 5,403,311 A | * | 4/1995 | Abele et al. ................... 604/21 |
| 5,458,597 A | * | 10/1995 | Edwards et al. ............... 604/21 |
| 5,472,441 A | * | 12/1995 | Edwards et al. ............. 128/898 |
| 5,542,916 A | | 8/1996 | Hirsch et al. |
| 5,554,110 A | | 9/1996 | Edwards et al. |
| 5,599,294 A | | 2/1997 | Edwards et al. |
| 5,964,727 A | | 10/1999 | Edwards et al. |

FOREIGN PATENT DOCUMENTS

WO    WO 99/18869    4/1999

* cited by examiner

*Primary Examiner*—Michael Peffley
(74) *Attorney, Agent, or Firm*—David Klein; Dekel Patent Ltd.

(57) ABSTRACT

An electrosurgical system including at least one electrically insulating sheath, at least one electrically conductive stylet slidingly disposed in the at least one sheath, the at least one stylet being connectable to and energizable by an electrical source, an actuator system connected to the at least one stylet and connected to the at least one sheath independently of the at least one stylet, wherein the actuator system moves the at least one stylet and the at least one sheath independently of each other.

8 Claims, 7 Drawing Sheets

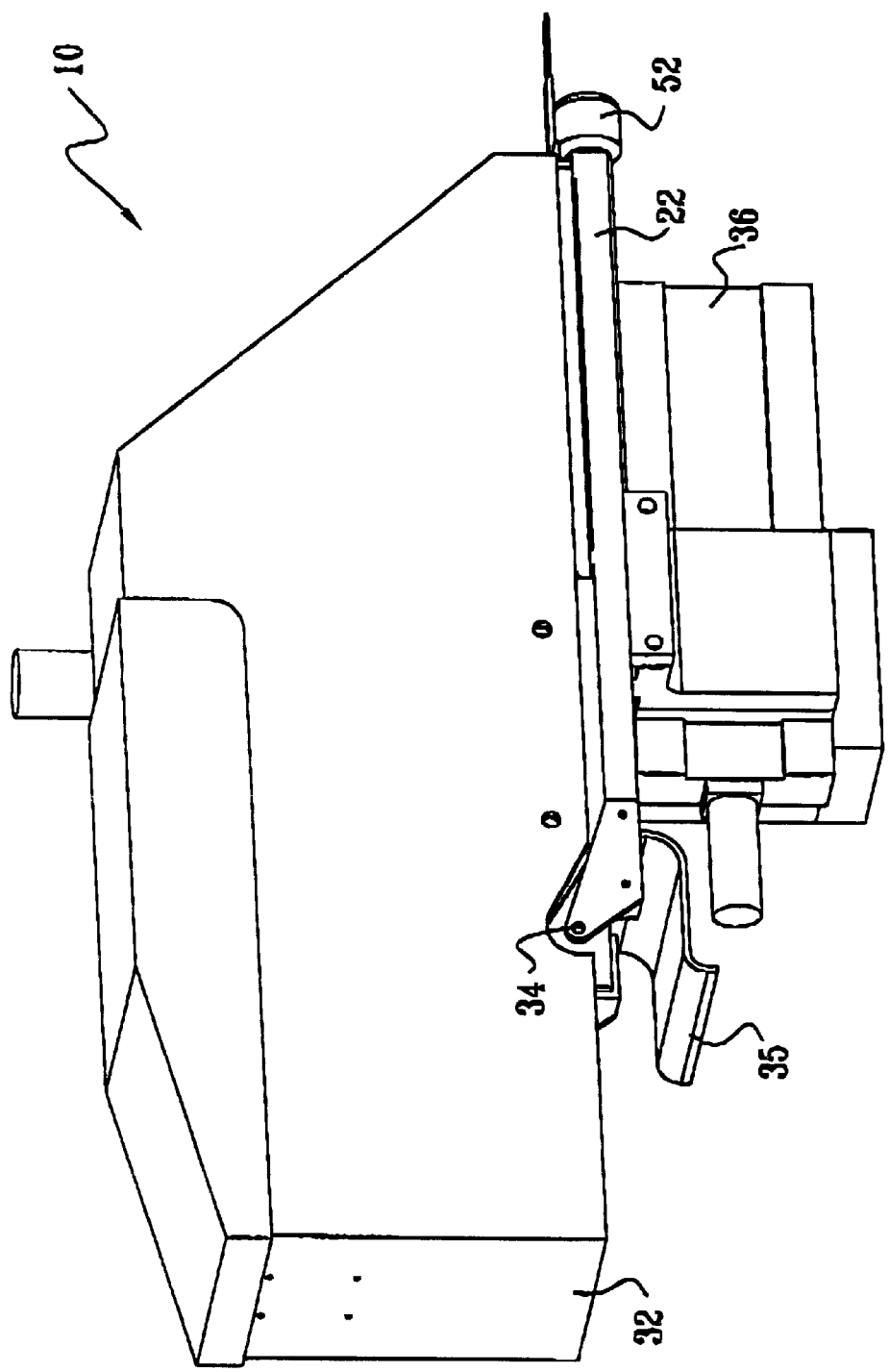

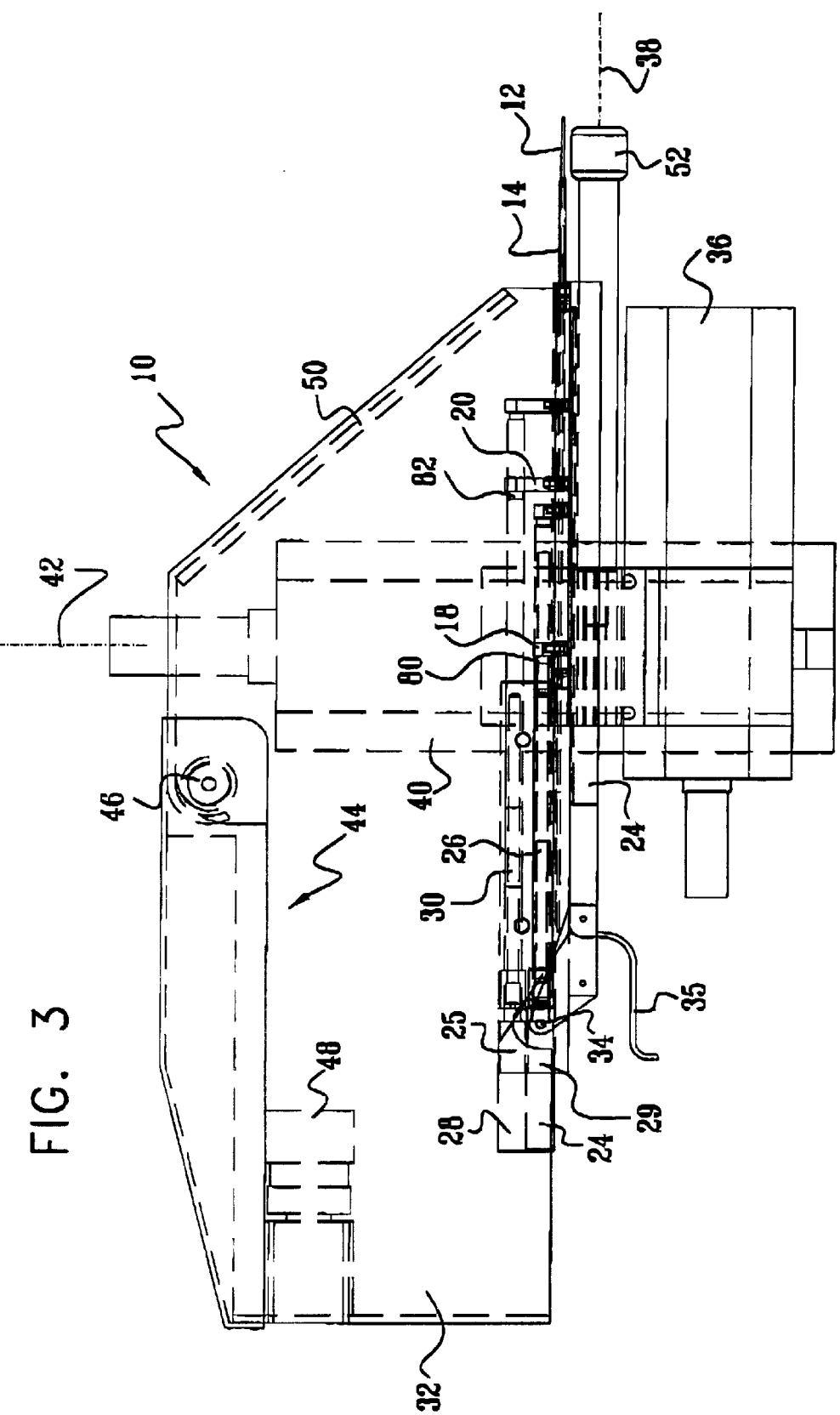

ELECTROSURGICAL SYSTEM

FIELD OF THE INVENTION

The present invention relates generally to a electrosurgical probe systems and particularly to such a system that includes an array of radio frequency (RF) electrodes with controllable, movable, non-conductive sleeves.

BACKGROUND OF THE INVENTION

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

The use of electrosurgical procedures in electrically conductive environments, however, can be problematic. For example, many procedures require flushing of the region to be treated with isotonic saline (also referred to as normal saline), both to maintain an isotonic environment and to keep the field of view clear. The presence of saline, which is a highly conductive electrolyte, can cause shorting of the electrosurgical electrode in both monopolar and bipolar modes. Such shorting causes unnecessary heating in the treatment environment and can further cause non-specific tissue destruction.

Prostate diseases, such as prostate cancer and benign prostatic hypertrophy (BPH), can cause enlargement of the prostate which in turn causes a narrowing of the urethra adjacent the prostate caused by swelling of the surrounding tissue. Such narrowing can cause difficulty in urination, resulting in discomfort and exposing the patient to further complications. A variety of methods have been proposed for treating enlarged prostates. Generally, the methods rely on either reducing the prostatic mass to lessen pressure on the urethra or resecting prostatic tissue adjacent the urethra in order to increase the luminal area for passing urine. The first group of methods include various protocols for directing energy, including microwave radiation, RF energy, and laser energy, to induce an increase in tissue temperature within a defined volume of the prostate. Such an increase in tissue temperature, often referred to as "thermotherapy", will be maintained at a temperature and for a time sufficient to cause necrosis of the treated prostatic tissue, with the necrosed tissue being subsequently sloughed off or reabsorbed into the surrounding tissue mass. Such sloughing off or reabsorption of the necrosed tissue, in turn, will cause size reduction of the prostate, relieving the symptoms of BPH. The latter group of methods includes the use of endoscopes introduced through the urethra which allow for controlled tissue resection.

Of particular interest to the present invention are invasive, catheter-like devices that are inserted into prostatic tissue. An example of such a device is described in U.S. Pat. No. 5,964,727 to Edwards et al., the disclosure of which is incorporated herein by reference. The Edwards et al. device includes a catheter having a stylet guide for directing a flexible stylet outward through a stylet port and through intervening tissue at a preselected, adjustable angle to a target tissue. In one embodiment, the stylet is an RF electrode with a non-conductive sleeve which is axially movable on the electrode to expose a selected portion of the electrode surface in the target tissue. However, the Edwards et al. device suffers from the drawback of lack of control of movement of the non-conductive sleeve.

SUMMARY OF THE INVENTION

The present invention seeks to provide an improved electrosurgical system that includes an array of RF electrodes (stylets) with controllable, movable, non-conductive sleeves. The electrosurgical system preferably includes an actuator system that can move the stylets and sheaths independently of each other. In this manner, the actuator system has two modes of operation. In a first mode, the actuator system moves the stylets together with the sheaths. In a second mode, the actuator system slides the stylets relative to the sheaths, thereby exposing more or less of the stylets as required for the electrosurgery procedure. An optical sensor system is preferably in electrical communication with the actuator system in a closed loop control system. The actuator system controls movement of the stylets and sheaths in accordance with feedback received from the optical sensor system, and commands received from a treatment plan, such as from treatment software.

It is noted that although the electrosurgical system of the present invention is described for use with prostate treatment, nevertheless the system of the present invention is not limited to the prostate but may be used for any kind of suitable body organ or cavity.

There is thus provided in accordance with a preferred embodiment of the present invention an electrosurgical system including at least one electrically insulating sheath, at least one electrically conductive stylet slidingly disposed in the at least one sheath, the at least one stylet being connectable to and energizable by an electrical source, an actuator system connected to the at least one stylet and connected to the at least one sheath independently of the at least one stylet, the actuator system having two modes of operation, wherein in a first mode the actuator system moves the at least one stylet together with the at least one sheath, and in a second mode the actuator system slides the at least one stylet relative to the at least one sheath.

In accordance with a preferred embodiment of the present invention the actuator system includes a first tab attached to the at least one stylet, a second tab attached to the at least one sheath, an actuator, and a plurality of arms attached to and movable by the actuator, the arms being selectively attachable to the first and second tabs.

Further in accordance with a preferred embodiment of the present invention a plurality of the stylets and sheaths are provided, wherein the first tab is attached to a pair of the stylets, and the second tab is attached to a pair of the sheaths, the pair of stylets being electrically energized as a bipolar electrode.

Still further in accordance with a preferred embodiment of the present invention the at least one stylet and sheath are slidingly mounted in a frame, and the plurality of arms are hingedly attached to the frame at a pivot, the plurality of arms being selectively swingable about the pivot away from and towards the first and second tabs.

Additionally in accordance with a preferred embodiment of the present invention the frame is attached to a first positioner that moves the frame in a first direction. The frame may also be attached to a second positioner that moves the frame in a second direction.

In accordance with a preferred embodiment of the present invention an optical sensor system is provided that detects movement of the at least one stylet and sheath, the optical sensor system being in electrical communication with the actuator system, wherein the actuator system controls movement of the at least one stylet and sheath in accordance with feedback received from the optical sensor system.

Further in accordance with a preferred embodiment of the present invention the optical sensor system includes a light source that illuminates at least one portion of the at least one stylet and sheath, and a camera that views and detects movement of the at least one portion.

Still further in accordance with a preferred embodiment of the present invention a mirror is mounted at an angle above the at least one portion of the at least one stylet and sheath, the mirror reflecting an image of the at least one portion towards the camera.

BRIEF DESCRIPTION OF THE DRAWINGS

The present invention will be understood and appreciated more fully from the following detailed description, taken in conjunction with the drawings in which:

FIGS. 2A and 2B are simplified pictorial illustrations of the electrosurgical system of FIGS. 1A and 1B, shown at a different perspective angle, in respective closed and open positions;

FIG. 3 is a simplified pictorial, partially sectional illustration of the electrosurgical system of FIGS. 1A and 1B;

DETAILED DESCRIPTION OF A PREFERRED EMBODIMENT

Reference is now made to FIGS. 1A–4 which illustrate an electrosurgical is system 10 constructed and operative in accordance with a preferred embodiment of the present invention.

Electrosurgical system 10 preferably includes one or more electrically conductive stylets 12 slidingly disposed in electrically insulating sheaths 14. Stylets 12 are preferably surgical grade electrodes electrically connected to a high frequency electrical source (not shown). Stylets 12 and sheaths 14 may be flexible along at least a portion of their lengths.

Figure 4:
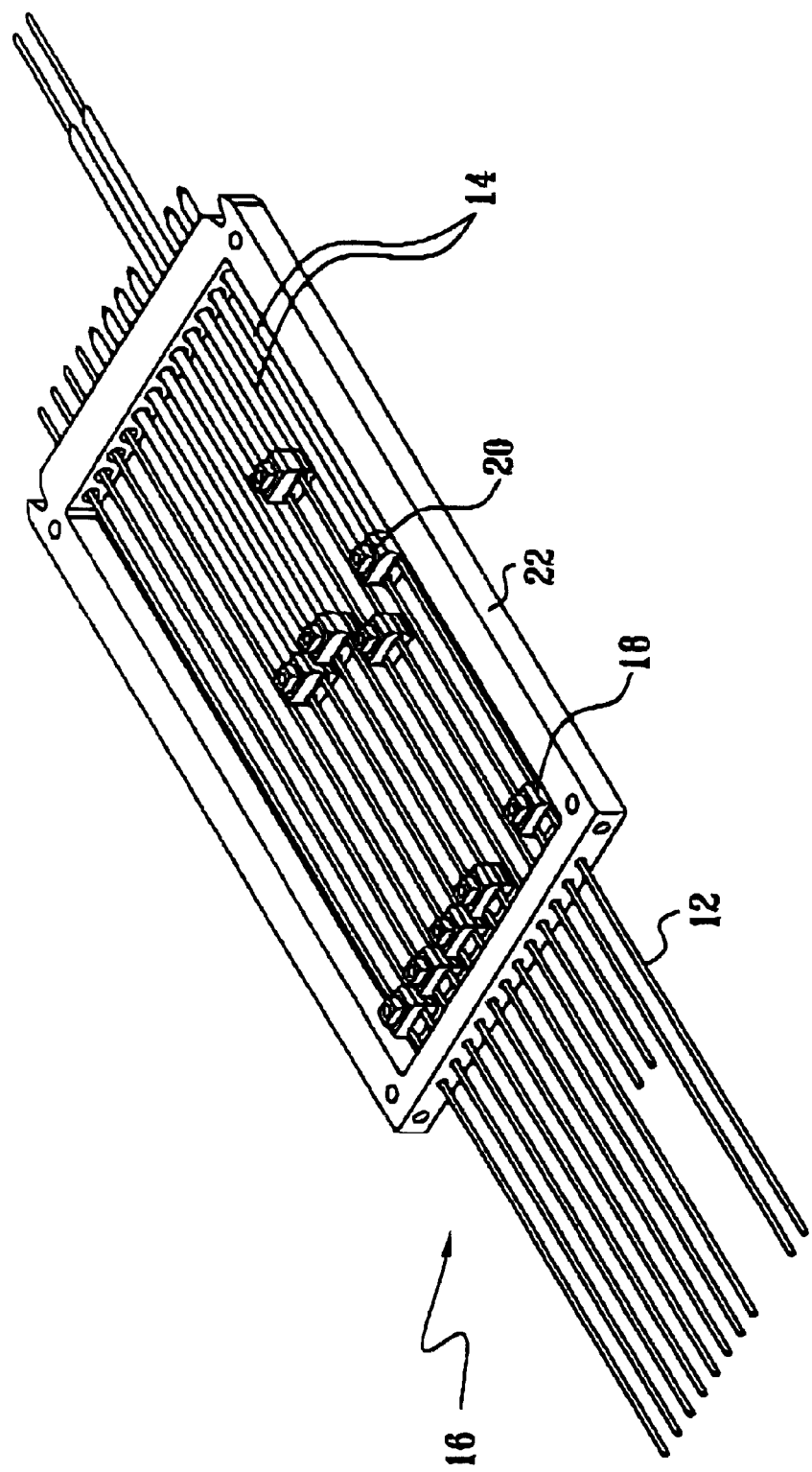
FIG. 4 is a simplified pictorial illustration of an array of electrosurgical probes used in the system of FIGS. 1A and 1B, constructed and operative in accordance with a preferred embodiment of the present invention.

An actuator system 16 is preferably connected to stylets 12, and connected to sheaths 14 independently of the connection to stylets 12. In other words, actuator system 16 can move stylets 12 and sheaths 14 independently of each other. As seen in FIG. 4, actuator system 16 preferably includes a first tab 18 attached to stylet 12, and a second tab 20 attached to sheath 14. Preferably first tab 18 is attached to a pair of stylets 12, and second tab 20 is attached to a pair of sheaths 14, the pair of stylets 12 being electrically energized as a bipolar electrode. Alternatively, each of tabs 18 and 20 can be attached to just one stylet 12 and sheath 14, with pairs of stylets 12 again being electrically energized as a bipolar electrode. As another alternative, stylets 12 can be used as monopolar electrodes, in conjunction with an external electrode (not shown). Stylets 12 and sheaths 14 are preferably slidingly mounted in a frame 22.

Figure 1A:
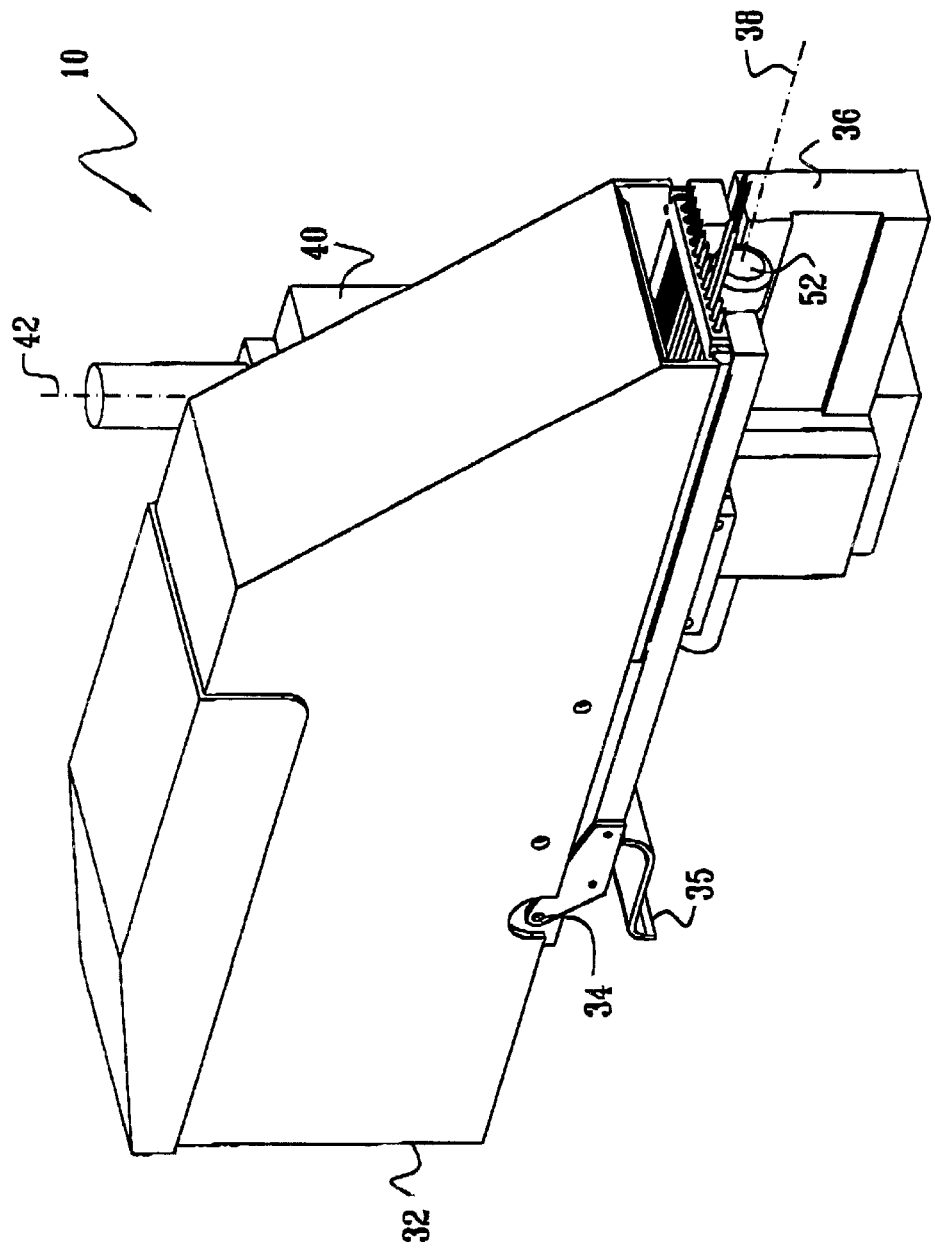
FIGS. 1A and 1B are simplified pictorial illustrations of an electrosurgical system constructed and operative in accordance with a preferred embodiment of the present invention, in respective closed and open positions.
Figure 1B:
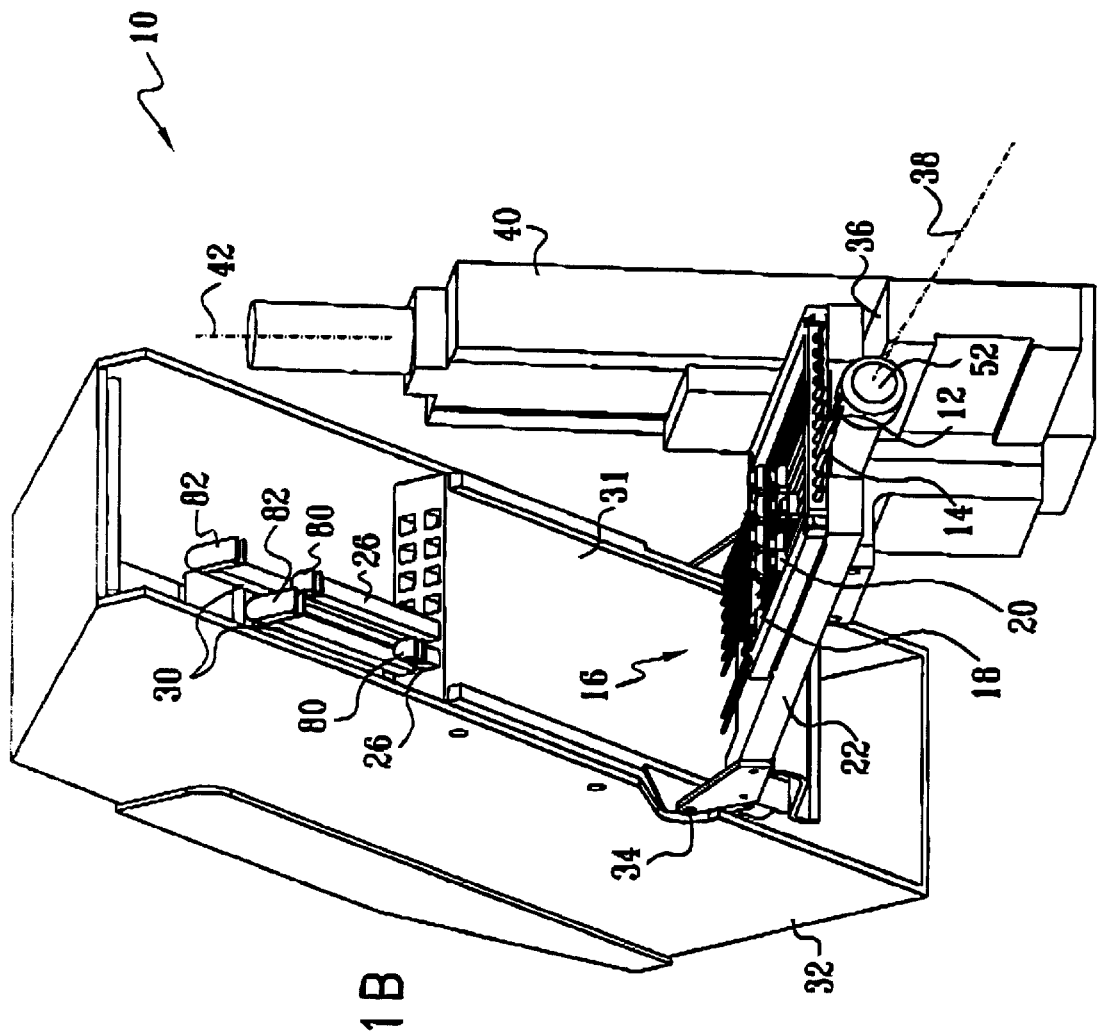
Figure 2B:
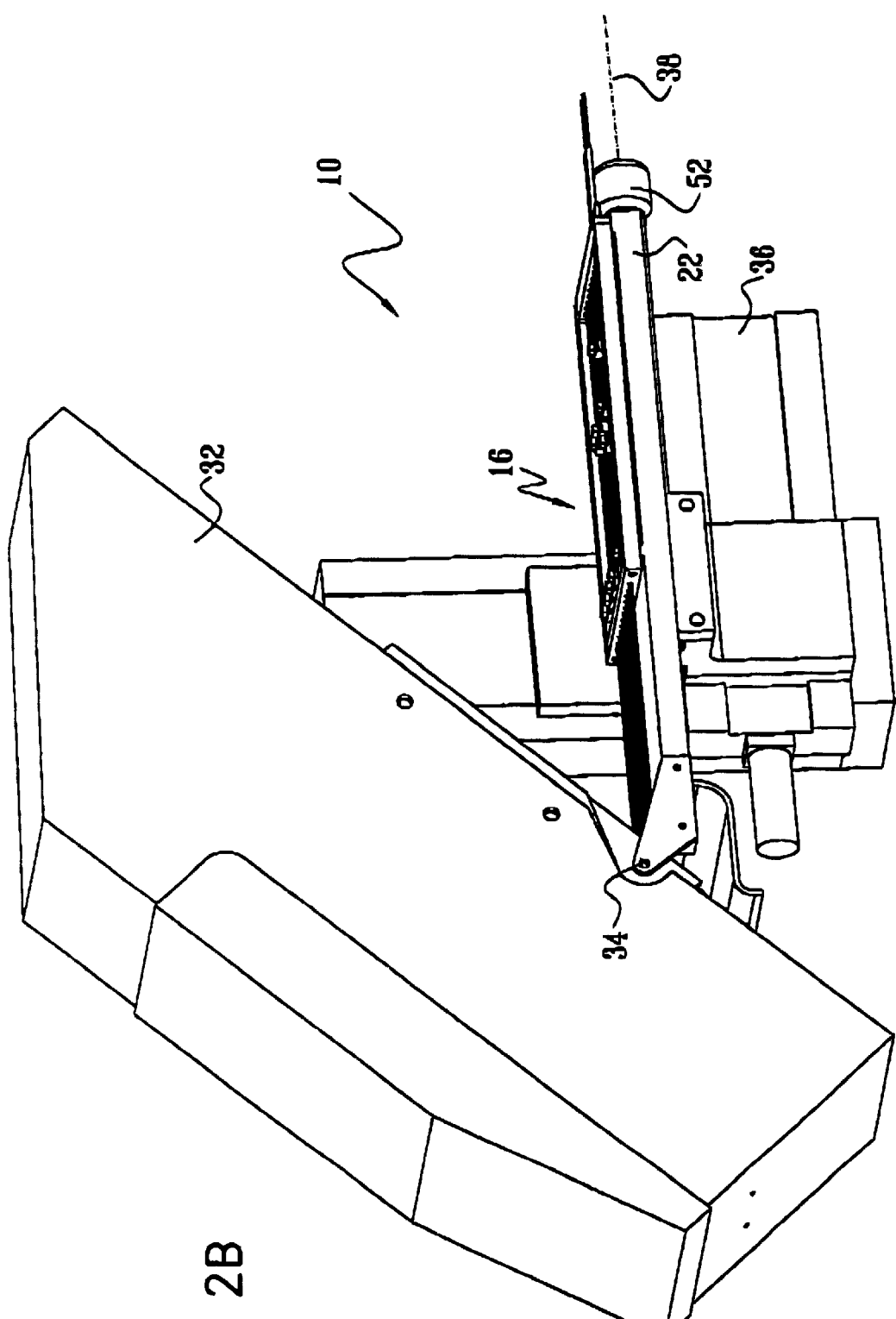

As seen best in FIGS. 1B and 3, actuator system 16 preferably includes an actuator 24 connected to one or more arms 26, and another actuator 28 connected to one or more arms 30. Actuators 24 and 28 and arms 26 and 30 are preferably disposed in an enclosure 31 (FIG. 1B), which is housed in a housing 32 preferably hingedly attached to frame 22 at a pivot 34. Arms 26 and 30 are arranged to grasp tabs 18 and 20, respectively, by means of grabbing elements, such as mechanical grabbing elements 80 and 82 attached to the arms 26 and 30, respectively, as shown in FIGS. 1B and 3. Arms 26 and 30, grabbing elements 80 and 82, together with housing 32, are selectively swingable about pivot 34 away from and towards tabs 18 and 20. In this manner, one can easily gain access to stylets 12 and sheaths 14 for replacement or disposal. Indeed the actuator system 16 as shown in FIG. 4 can be constructed as a disposable cartridge, together with disposable stylets 12 and sheaths 14. It is appreciated that actuator system 16 can be alternatively constructed such that arms 26 and 30 can be moved linearly or in other manners away from and towards tabs 18 and 20. Wires (not shown) leading from stylets 12 to the electrical source (not shown), can be gathered and fed over a curved guide member 35, mounted on a rear portion of frame 22.

Actuators 24 and 28 preferably moves stylets 12 and sheaths 14 independently of each other. In this manner, actuator system 16 has two modes of operation. In a first mode, actuator system 16 moves stylets 12 together with sheaths 14. In a second mode, actuator system 16 slides stylets 12 relative to sheaths 14, thereby exposing more or less of stylets 12 as required for the electrosurgery procedure. Linear encoders 25 and 29 (FIG. 3) may be provided for monitoring and controlling the position of actuators 28 and 24, respectively.

Frame 22 is preferably attached to a first positioner 36 that moves frame 22 in a first direction, such as generally along a longitudinal axis 38. In the illustrated embodiment, first positioner 36 may be a linear actuator. Alternatively, first positioner 36 may be a step motor, and can rotate frame 22 about axis 38. Frame 22 is also preferably attached to a second positioner 40 that moves frame 22 in a second direction, such as generally along a vertical axis 42, generally perpendicular to axis 38. Again, in the illustrated embodiment, second positioner 40 may be a linear actuator. Alternatively, second positioner 40 may be a step motor, and can rotate frame 22 about axis 42.

In accordance with a preferred embodiment of the present invention, electrosurgical system 10 includes an optical sensor system 44 that detects movement of stylets 12 and sheaths 14. Optical sensor system 44 is preferably in electrical communication with actuator system 16 in a closed loop control system. Actuator system 16 preferably controls movement of stylets 12 and sheaths 14 in accordance with feedback received from optical sensor system 44, and commands received from a treatment plan (which may be fed from treatment software, not shown).

Optical sensor system 44 preferably includes a light source 46 that illuminates one or more portions of stylets 12 and sheaths 14, and a camera 48 that views and detects movement of those portions of stylets 12 and sheaths 14. Alternatively or additionally, ambient light or sunlight can be used for illumination. Preferably a mirror 50 is mounted at an angle above stylets 12 and sheaths 14. Mirror 50 reflects an image of those portions of stylets 12 and sheaths 14 which are to be monitored, towards camera 48.

Figure 5:
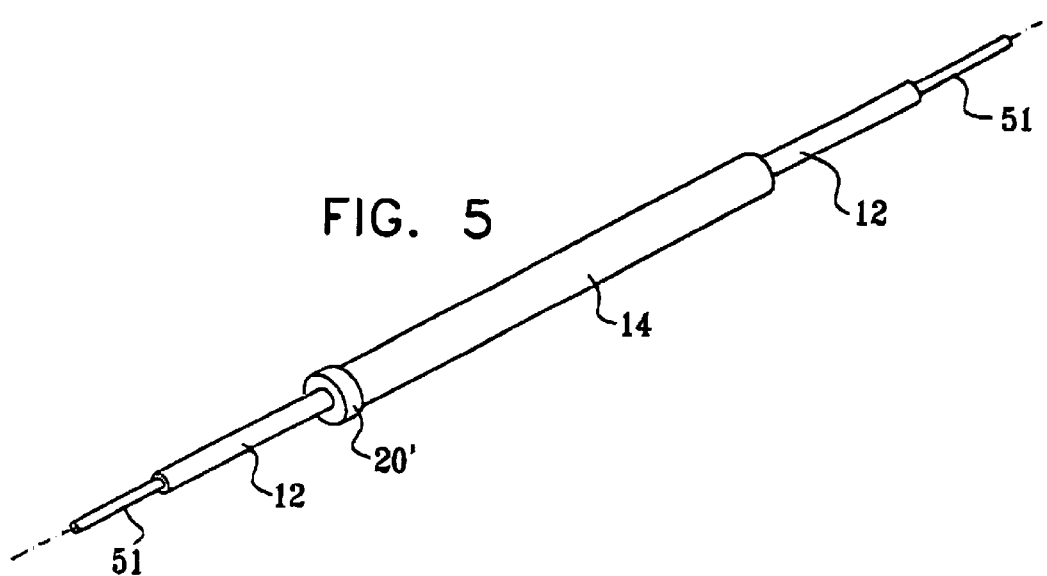
FIG. 5 is a simplified pictorial illustration of another type of electorosurgical probe, constructed and operative in accordance with another preferred embodiment of the present invention.

Reference is now made to FIG. 5 which illustrates that in accordance with another preferred embodiment of the present invention, stylet 12 can be formed as a hollow needle and an optical fiber 51 can be passed through stylet 12. Optical fiber 51 can be used to illuminate and view regions of interest. In addition, optical fiber 51 can be used to activate certain light-activated chemical therapy agents, by delivering light energy to the area where such chemical therapy agents have been administered. In accordance with this embodiment of this invention, a ring-shaped tab 20' is preferably attached to the sheath 14, as shown in FIG. 5.

Electrosurgical system 10 may be used in conjunction with a transrectal ultrasound probe 52 (FIGS. 1A–3) or a transurethral endoscope (not shown), both of which are in electrical communication with actuator system 16 and optical sensor system 44. Additionally, cooling apparatus (not shown) may be provided for supplying cooling fluid through the urethra during treatment procedure.

Figure 6:
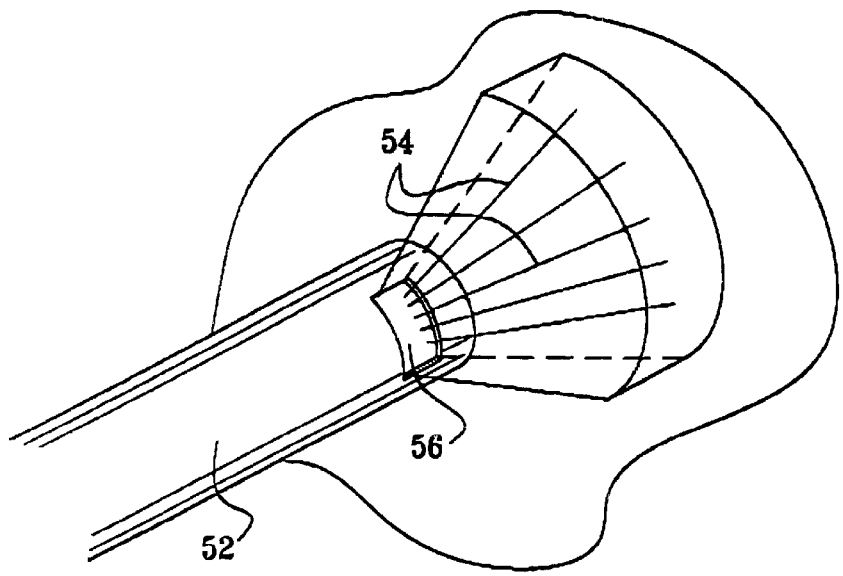
FIG. 6 is a simplified pictorial illustration of the use of a transrectal ultrasound for mapping and monitoring a treatment zone, in accordance with a preferred embodiment of the present invention.

Reference is now made to FIG. 6 which illustrates use of transrectal ultrasound probe 52 in mapping and monitoring a treatment zone, in accordance with a preferred embodiment of the present invention. Before commencing treatment of, for example, a prostate, with stylets 12 and sheaths 14, probe 52 is preferably inserted in the rectum of the patient in order to obtain a three-dimensional mapping of the target zone. FIG. 6 shows beams 54 of ultrasonic energy delivered through a window 56 in probe 52 to the zone of interest. Probe 52 is preferably advanced and/or retracted to different positions in the rectum so as to provide "slices" of mapping data which are combined to provide an overall three-dimensional mapping of the target zone. The mapping data is used to determine preferred positions of stylets 12 and sheaths 14. After stylets 12 and sheaths 14 have been introduced to the target zone, probe 52 continues to provide positional information to monitor and verify the correct position of stylets 12 and sheaths 14 during treatment. Of course other devices, such as an external optical encoder, can be used instead of or in conjunction with probe 52.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An electrosurgical system comprising:
   at least one electrically insulating sheath;
   at least one electrically conductive stylet slidingly disposed in said at least one sheath, said at least one stylet being connectable to and energizable by an electrical source;
   and an actuator system connected to said at least one stylet and connected to said at least one sheath independently of said at least one stylet, wherein said actuator system moves said at least one stylet and said at least one sheath independently of each other;
   wherein said actuator system has two modes of operation, wherein in a first mode said actuator system moves said at least one stylet together with said at least one sheath, and in a second mode said actuator system slides said at least one stylet relative to said at least one sheath, and wherein said actuator system comprises a first tab attached to said at least one stylet, a second tab attached to said at least one sheath, an actuator, and a plurality of arms attached to and movable by said actuator, said arms being selectively attachable to said first and second tabs.

2. The electrosurgical system according to claim 1 and further comprising a plurality of said stylets and sheaths, wherein said first tab is attached to a pair of said stylets, and said second tab is attached to a pair of said sheaths, the pair of stylets being electrically energized as a bipolar electrode.

3. The electrosurgical system according to claim 1 wherein said at least one stylet and sheath are slidingly mounted in a frame, and wherein said plurality of arms are hingedly attached to said frame at a pivot, said plurality of arms being selectively swingable about said pivot away from and towards said first and second tabs.

4. The electrosurgical system according to claim 3 wherein said frame is attached to a first positioner that moves said frame in a first direction.

5. The electrosurgical system according to claim 4 wherein said frame is attached to a second positioner that moves said frame in a second direction.

6. An electrosurgical system comprising:
   at least one electrically insulating sheath;
   at least one electrically conductive stylet slidingly disposed in said at least one sheath, said at least one stylet being connectable to and energizable by an electrical source;
   an actuator system connected to said at least one stylet and connected to said at least one sheath independently of said at least one stylet, wherein said actuator system moves said at least one stylet and said at least one sheath independently of each other; and
   an optical sensor system that detects movement of said at least one stylet and sheath, said optical sensor system being in electrical communication with said actuator system, wherein said actuator system controls movement of said at least one stylet and sheath in accordance with feedback received from said optical sensor system.

7. The electrosurgical system according to claim 6 wherein said optical sensor system comprises a light source that illuminates at least one portion of said at least one stylet and sheath, and a camera that views and detects movement of said at least one portion.

8. The electrosurgical system according to claim 7 and further comprising a mirror mounted at an angle above said at least one portion of said at least one stylet and sheath, said mirror reflecting an image of said at least one portion towards said camera.

\* \* \* \* \*